(12) United States Patent
Morris et al.

(10) Patent No.: US 6,886,565 B2
(45) Date of Patent: May 3, 2005

(54) MACULA COVER AND METHOD

(75) Inventors: Robert E. Morris, Birmingham, AL (US); Clark D. Witherspoon, Birmingham, AL (US); W. Brad Priester, Memphis, TN (US)

(73) Assignee: Innovative Retinal Products LLC, Birmingham, AL (US)

( * ) Notice: Subject to any disclaimer, the term of this patent is extended or adjusted under 35 U.S.C. 154(b) by 133 days.

(21) Appl. No.: 10/274,284

(22) Filed: Oct. 18, 2002

(65) Prior Publication Data

US 2003/0156252 A1 Aug. 21, 2003

Related U.S. Application Data

(60) Provisional application No. 60/343,608, filed on Oct. 19, 2001.

(51) Int. Cl.[7] .................................... A61F 13/00
(52) U.S. Cl. .................. 128/846; 128/858; 128/898; 623/6.63; 606/107; 604/289
(58) Field of Search ................. 128/846, 858, 128/898, 857; 623/6.63, 4.1, 5.11; 606/4, 5, 6, 107; 604/28, 521, 289, 294, 302, 304, 290

(56) References Cited

U.S. PATENT DOCUMENTS

| 4,646,720 A | * | 3/1987 | Peyman et al. | ............. | 128/898 |
| 5,527,356 A | | 6/1996 | Peyman et al. | | |
| 5,695,492 A | | 12/1997 | Brown | | |
| 5,941,250 A | * | 8/1999 | Aramant et al. | ............. | 128/898 |
| 6,024,719 A | * | 2/2000 | Morris | ......................... | 604/28 |
| 6,135,118 A | * | 10/2000 | Dailey | ......................... | 128/898 |
| 6,159,218 A | * | 12/2000 | Aramant et al. | ............. | 606/107 |
| 6,210,357 B1 | * | 4/2001 | Morris | ......................... | 604/28 |
| 6,612,311 B2 | * | 9/2003 | Dailey | ......................... | 128/898 |

FOREIGN PATENT DOCUMENTS

| EP | 0 363 811 A1 | 4/1990 |
| EP | 0 482 340 A1 | 4/1992 |
| WO | WO 00/59396 | 10/2000 |

OTHER PUBLICATIONS

Yanoff, Kurata, Lamensdorf: "Inexpensive device to reduce surgical light exposure," Ophthamology–Instrument and Book Supplement 1983, vol., 90, pp. 137–138, 1983, XP008019398.

* cited by examiner

Primary Examiner—Fadi H. Dahbour
(74) Attorney, Agent, or Firm—Jones Day (57) ABSTRACT

A macula cover having a flexible sheet member and including an contact surface, an outer surface, a perimeter, and an annular stiffener. The sheet member is sized to cover the fovea and the parafoveal area of the macula during retinal surgery.

13 Claims, 6 Drawing Sheets

MACULA COVER AND METHOD

RELATED APPLICATIONS

The present application claims priority under 35 U.S.C. 119(e) to U.S. Provisional Application No. 60/343,608, filed Oct. 19, 2001, which is incorporated herein by reference.

TECHNICAL FIELD

The field of the present invention relates generally to ocular surgical devices and procedures

BACKGROUND OF THE INVENTION

Ophthalmologists routinely treat patients that suffer from impaired vision caused by a condition known as traction maculopathy. This condition, which is the result of tractional forces that distort or wrinkle the center of the retina (macula), may affect as many as 2.5 million patients. Moreover, traction maculopathies, in the form of vitreomacular traction syndrome, cellophane maculopathy, epimacular proliferation, and macular hole disease, are said to occur in 6.4% of the U.S. population over 50 years of age.

For some time, ophthalmologists have recognized the effectiveness of treating traction maculopathy with surgical intervention. In the surgical procedure, the eye surgeon performs a series of surgical steps that eliminate the tractional forces from the macula. Recently, with the development of advanced high-powered surgical microscopes, and other modern surgical techniques, such as the Indocyanine Green (ICG) staining technique of the internal limiting membrane, surgeons have been able to execute surgical manipulations on tissues of the macula that were previously difficult to visualize.

The use of modern surgical techniques, however, creates additional concerns that a surgeon must keep in mind while completing a surgical procedure to reduce tractional forces on the macula. When macular surgery is performed, the surgeon must use an endoscopic light probe that produces high-powered illumination. Because there is no absorbing barrier between this light source and the retina, this illumination can damage the retina. F. Kuhn, R. E. Morris, & M. P. Massey, "Photic Retinal Injury from Endoillumination during Victrectomy," American Journal of Ophthalmology, 111:42–46 (January, 1991). Such damage to the retinal tissues is referred to as phototoxicity or photic retinopathy.

The damaging effect of medical instrument illumination has been recognized for three decades. In 1973, Tso described photic retinopathy lesions that were intentionally produced in the eyes of a monkey. M. Tso, Investigative Ophthalmology, 12: 17–34 (1973). Later, McDonald and Irvine described a group of patients after cataract extraction that had similar lesions. H. R. McDonald & A. R. Irvine, Ophthalmology, 90: 945–951 (1983). Such lesions have also been intentionally demonstrated by experiments that exposed human eyes, prior to the removal of the eye for an unrelated malignant tumor, to an operating microscope light for sixty minutes. W. R. Green W R & D. M. Robertson, American Journal of Ophthalmology, 112: 520–527 (1991).

The prevalence rate of retinal phototoxicity has been estimated to range from 3% to 7.4% after surgery for cataract extraction using the illuminated microscope. S. G. Khwarg, F. A. Linstone, S. A. Daniels, et al., American Journal of Ophthalmology, 103: 255–263 (1987); J. E. Gomolin & R. K. Koehekoop, Canadian Journal of Ophthalmology, 28: 2121–224 (1993). Even if a characteristic retinal burn is not present, it has been postulated that subtle, chronic cystoid macular edema may result. At its worst, phototoxicity can produce permanent legal blindness in the affected eye.

Normal physiological protection of the human retina against phototoxicity is partly provided by the ocular media, which filters or absorbs the most damaging ultraviolet rays. The pupil is also capable of constricting in response to bright light, thus reducing light transmission to the retina by more than 80%. R. E. Records & J. L. Brown, Adaptation in Duane's Foundations of Clinical Ophthalmology, vol.2, ch. 16, Tasmas and Jaeger Editors (1991). Finally, if light is too intense, the eyelids will close, or the brain may turn the gaze of the eyes away from the offending light source. Unfortunately, during macular surgery, all of these protecting mechanisms are bypassed.

For over twenty years, various efforts have been made to understand and prevent phototoxicity during eye surgery. The filtering of shorter wavelength light lessens but does not eliminate retinal damage. R. H. Keates & P. R. Armstrong, Ophthalmic Surgery, 16: 40–41 (1985). Similarly, the filtering of infrared light greater than 700 nanometers is only partially helpful. M. A. Mainster, W. T. Ham, F. C. Dehori, Ophthalmology, 90: 927–932 (1983). Directing the endoscopic light probe away from the macula as much as possible, keeping the light probe as far from the macular surface as possible, and decreasing the endoscopic light intensity are the variables the surgeon can control.

Specifically, there is also the continued concern that the use of high intensity light may cause phototoxic injury to the foveal and macular tissues. Additionally, there remains a concern that the use of chemicals, such as Indocyanine Green (ICG) staining to identify intraocular structures may expose the foveal and macular tissues to injury from chemical toxicity.

SUMMARY OF THE INVENTION

The present invention is directed to a macula cover for the protection of the macula during eye surgery. The macula cover includes a sheet member made from a flexible material. The sheet member includes an contact surface, an outer surface, a perimeter, and an annular stiffener.

In a first separate aspect of the present invention, the macula cover further includes a sheet member that is sized to cover the fovea and parafoveal area of the macula and is radially tapered toward the perimeter. The perimeter defines a knife edge and the contact surface is positionable over and in contact with the surface of the fovea and parafoveal area of the macula.

In a second separate aspect of the present invention, the macula cover may include a tab that extends from the perimeter of the sheet member. The tab would be attached at its periphery to the periphery of the sheet member.

In a third separate aspect of the present invention, a macula cover may include a tab that extends from the center of the sheet member. The tab would be attached to the center of the convex surface of the sheet member.

In a fourth separate aspect of the present invention, the macula cover is contemplated to include the sheet member being made of an opaque material.

In a fifth separate aspect of the present invention, the macula cover may include an annular stiffener that includes a circular ridge and a sloping surface that extends between the circular ridge and the perimeter.

In a sixth separate aspect of the present invention, the macula cover may include a bioadhesive region on the perimeter of the inner surface of the sheet member.

In a seventh separate aspect of the present invention, a surgical method includes placing a macula cover over the macula and performing an ocular surgery with the macula covered.

In an eighth separate aspect of the present invention, a surgical tool kit includes a macula cover and an injector for the placement of the macula cover. The macular cover includes a sheet member made from a flexible material, an contact surface, an outer surface, a perimeter, and an annular stiffener. The injector includes a hollow tube, an opening, and an injector rod.

In a ninth separate aspect of the invention, a surgical tool kit includes a macula cover and an injector for the placement of the macula cover. The macula cover includes a flexible sheet member, an inner surface, a convex surface, a perimeter, a central tab, a plurality of radial elements and a bioadhesive region. The injector includes a hollow tube, an opening, an injector rod, and an injector forcep.

In a tenth separate aspect of the invention, combinations for increased advantage of any of the foregoing aspects and features are contemplated.

Accordingly, it is an object of the present invention to provide improved ocular procedures and devices therefor.

DETAILED DESCRIPTION OF THE PREFERRED EMBODIMENTS

The preferred embodiments will now be described with reference to the drawings. To facilitate description, element numerals designating an element in one figure will represent the same element in any other figure.

Figure 1:
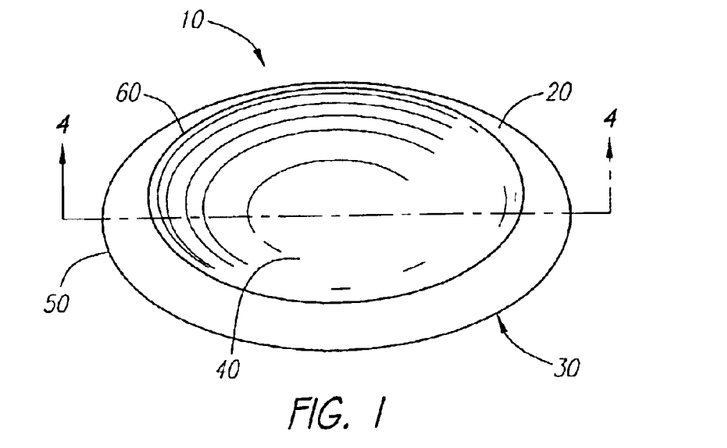
FIG. 1 is a perspective view of a macula cover.

Turning in detail to the figures, a macular cover 10 is shown including a flexible sheet member 20 with a contact surface 30, an outer surface 40, a perimeter 50, and an annular stiffener 60. The sheet member 20 is sized to cover the fovea and parafoveal area of the macula and the shape is generally circular. When the sheet member 20 is placed over the fovea and parafoveal area of the macula, the sheet member 20 extends radially from the central region of the fovea beyond the perimeter boundary of the parafoveal area of the macula. Other embodiments are contemplated wherein the cover may be sized to cover different sized regions of the central macula.

Figure 4:
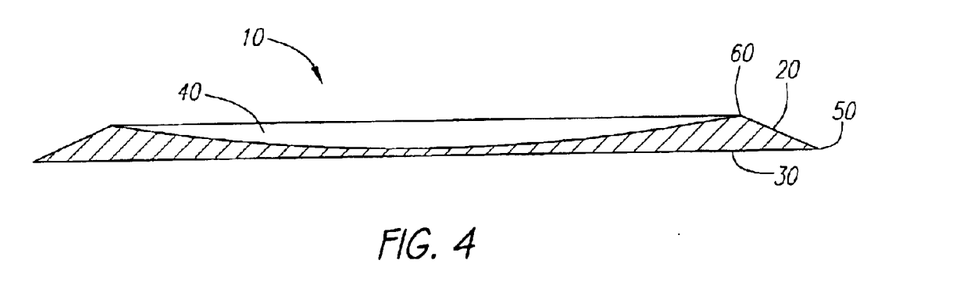
FIG. 4 is a cross-section view of a macula cover.

The sheet member 20 is radially tapered toward the perimeter 50. The radial tapering of the sheet member 20 is defined by a sloping incline surface that extends between the annular stiffener 60 to the perimeter 50 of the sheet member 20. The radial tapering creates an inclined surface that is designed to aid in maintaining the location of the macula cover 10 when it is placed over the fovea and parafoveal area of the macula. During the surgical procedure, the surgeon typically injects fluid into the eye. If the fluid is injected directly toward the macula cover 10, the injected fluid will make contact with the sloping incline surface that extends between the annular stiffener 60 and the perimeter 50. As the fluid passes over the inclined surface, the fluid generates downward pressure that is transferred through the sheet member 20. This transfer of the downward pressure on the sheet member 20 helps to maintain the position of the macula cover 10 over the macula during surgical irrigation.

The contact surface 30 of the sheet member 20 is positionable over and in contact with the surface of the fovea and parafoveal area of the macula. When the sheet member 20 in placed over the fovea and parafoveal area of the macula, the contact surface 30 makes direct contact with the surface of the fovea and parafoveal area of the macula and sits directly in contact with the cells of the macula. This direct contact is aided by the flexibility of the sheet member 20. As the contact surface 30 comes in contact with concave surface of the retina, the sheet member 20 flexes and bends to match the inner contours of the retinal surface.

The outer surface 40 of the sheet member 20 is configured to have a concave surface extending from the central region of the sheet member 20 to the annular stiffener 60. As the outer surface 40 extends to the annular stiffener 60, the outer surface 60 gradually increases upward forming a concave surface that extends to the circular ridge of the annular stiffener 60. The concave shape of the outer surface 40 of the sheet member 20 is designed to aid in the flexibility of the macula cover 10. The macula cover 10 is flexible in the central region of the sheet member 20 that extends to from the central region to the annular stiffener 60. This flexibility allows the contact surface 30 of the sheet member 20 to deform to surface irregularities that may exist on the surface of the macula. When the sheet member 20 is placed over the fovea and parafoveal area of the macula, there may be bumps and other irregularities and the contact surface 30 makes direct contact with these bumps and irregularities. The flexible concave configuration of the outer surface 40 of the sheet member 20 allows the contact surface 30 to flex over the irregularities maintaining contact with these surfaces and protecting the tissues of the macula.

The perimeter 50 of the sheet member 20 defines a knife-edge. The knife-edge is designed to provide a smooth transition between the surface of the retina and the outer surface 40 of the sheet member 20 of the macula cover 10. This smooth transition allows surgical fluids that are injected onto the surface of the retina to pass smoothly from the surface of the retina to the tapered region of the outer surface 40 of the sheet member 20. As the fluids flow over the knife-edge of the perimeter 50, the fluids pass onto the tapered region of the outer surface 40 and generate downward pressure. The downward pressure aids in stabilizing the macula cover 10 over the macula and preventing the repositioning of the macula cover 10 from fluid injection.

The annular stiffener 60 of the sheet member 20 is designed to provide a stiffening section that will maintain the macula cover 10 in a fully extended position. When the macula cover 10 is placed in the eye through an injector 70, the macula cover 10 is rolled along an axis that allows the macula cover 10 to be placed within a hollow tube 80. When the macula cover 10 is pushed through the hollow tube 80 by the injector rod 90, the macula cover exits through the opening 100 of the hollow tube 80 in a rolled configuration. The annular stiffener 60 is designed to aid in the expansion of the macula cover 10 by providing a spring effect to the sheet member 20. As the sheet member 20 begins to expand to a fully extended position, the annular stiffener 60 maintains the fully extended configuration by providing a stiff region that prevents the sheet member 20 of the macula cover 10 from folding over upon itself.

In a preferred embodiment, the sheet member 20 can be made from a medical grade plastic that is flexible and opaque. Other appropriate materials are also contemplated. The flexibility of the sheet member 20 allows the sheet member to be rolled up for placement in the injector 70 while the stiffness provided by the annular stiffener 60 provides enough stiffness to allow the flexible material to unfold and expand to cover the surface of the fovea and parafoveal area of the macula. The opaque properties of the sheet member 20 prevent any light from penetrating into the tissues of the macula.

In another embodiment, the sheet member 20 can also be made from two or more different materials that have differing densities. When the sheet member 20 is made from more than one material, the central area can be made from a material that has a greater density than the material used for the outer area. Examples of such materials include thin metals made from aluminum alloys, steel alloys, and other exotic metals. In this configuration, the sheet member 20 can be manufactured with an outer area that can be flexible and less dense than the central area. The less dense outer area can be made from medical grade plastics, silicones, and latex. The dual material configuration aids in the stabilization of the macula cover 10 by providing additional weight in the central region. This centrally located weight creates a down force that helps to keep the macula cover 10 in place while the flexible material allows the macula cover 10 to be rolled up for placement over the fovea and parafoveal area of the macula.

Figure 2:
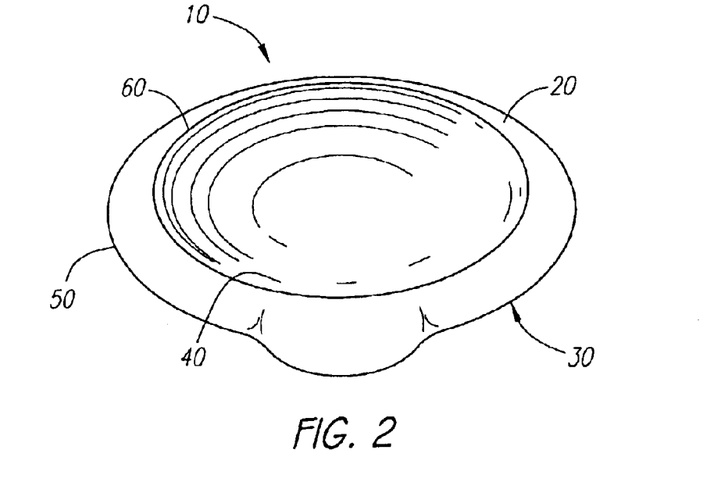
FIG. 2 is a perspective view of a macula cover with a peripheral tab.

In another embodiment, as shown in FIG. 2, the macula cover 10 includes a sheet member 20 that has an extended tab 110 attached at the periphery of the tab 110 to the periphery of the sheet member 20. The tab 110 is oblong shaped and extends away from the knife-edge of the perimeter 50 in the same plane as the sheet member 20. In use, the tab 110 is designed to aid in the removal of the macular cover 10 after the completion of the surgical procedure. When the surgeon completes surgery, he can remove the macula cover 10 by utilizing a pair of intraocular forceps and grasping the macula cover 10 by the extended tab 110.

In another embodiment, as shown in FIGS. 6–10, the macula cover can be part of a surgical tool kit that includes the macula cover 10 and an injector 70. The injector includes a hollow tube 80, an injector rod 90, and an opening 100. The hollow tube 80 is sized to contain the macula cover 10 when the macula cover 10 is rolled about an axis that extends longitudinally of the hollow tube 80. When the macula cover 10 is rolled on its longitudinal axis, the macula cover fits within the hollow tube 80 of the injector 70. After the injector 70 has been positioned within the eye over fovea and parafoveal area of the macula, the surgeon can manipulate the injector 70 to move the injector rod 90 longitudinally within the hollow tube 80. As the injector rod 90 moves longitudinally within the hollow tube 80, the injector rod 90 makes contact with the macula cover 10 and moves the macula cover 10 toward the end of the hollow tube 80 of the injector 70. The end of the hollow tube 80 has an opening 100 that allows the macula cover 10 to pass out of the interior of the hollow tube 80. The injector 70 allows the surgeon to place the macula cover 10 over the fovea and parafoveal area of the macula without exposing the macula cover 10 to contact with the surface of the conjunctiva. This allows the surgeon to use a sterile macula cover 10 that remains sterile during the placement of the cover within the eye.

Figure 3:
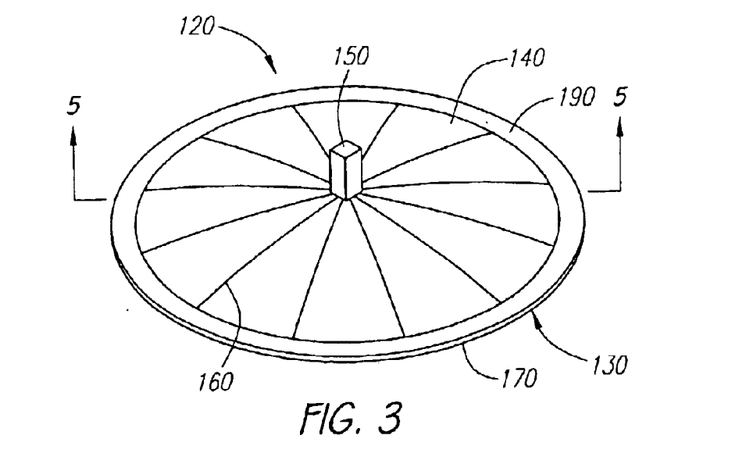
FIG. 3 is a perspective view of a macula cover in an umbrella configuration.
Figure 5:
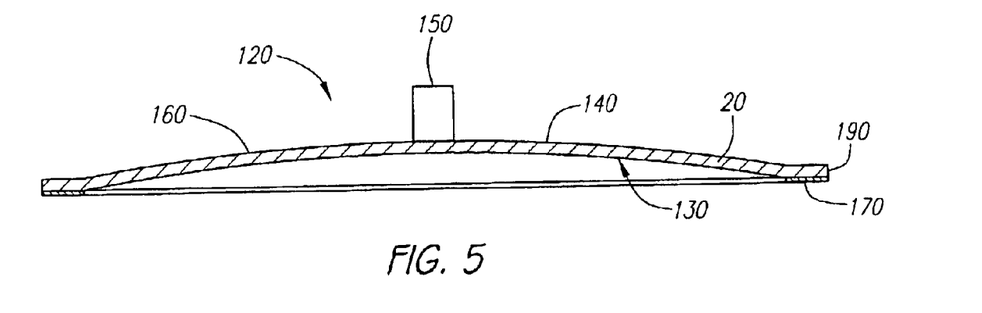
FIG. 5 is a cross-section view of a macula cover in an umbrella configuration.
Figure 6:
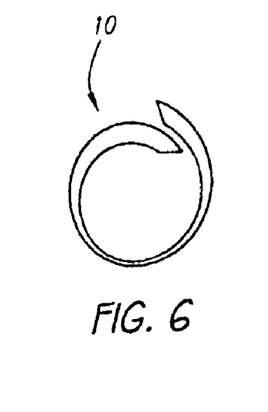
FIG. 6 is a side view of a macula cover rolled about an axis that allows the placement of the macula cover within the injector.
Figure 7:
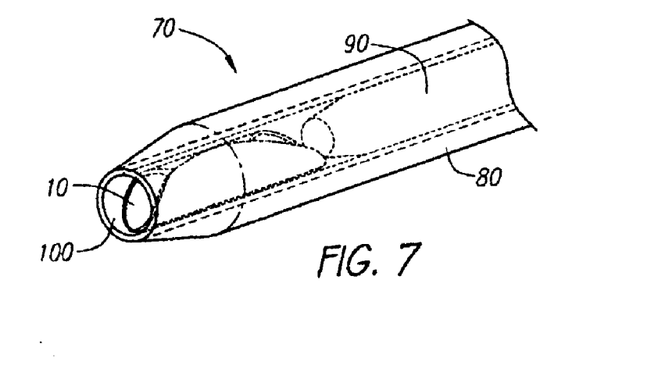
FIG. 7 is a perspective view of the injector with the macula cover contained within the injector.
Figure 8:
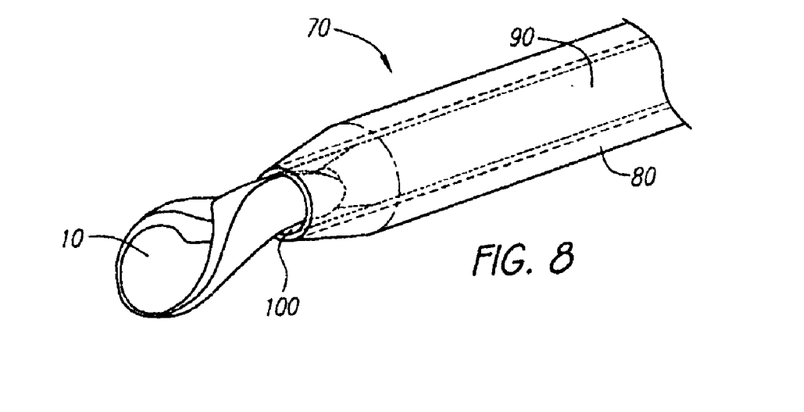
FIG. 8 is a perspective view of the injector with the macula cover exiting the injector and the injector rod partially deployed.
Figure 9:
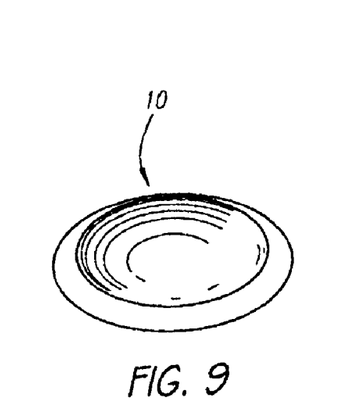
FIG. 9 is perspective view of a macula cover after the macula cover has exited the injector.
Figure 10:
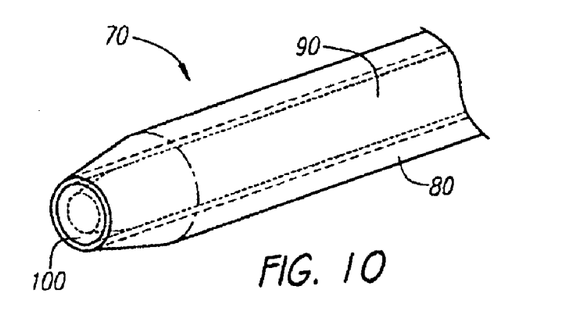
FIG. 10 is perspective view of the injector and the injector rod fully deployed.

In another embodiment, as shown in FIGS. 3 and 5, a macular cover 120 is shown in an umbrella configuration. The macula cover 120 in the umbrella configuration includes a flexible sheet member 20 with an inner surface 130, a convex surface 140, a perimeter 190, a central tab 150 and a plurality of radial elements 160. The sheet member 20, which is generally circularly shaped, is sized to cover the fovea and parafoveal area of the macula. When the sheet member 20 is placed over the fovea and parafoveal area of the macula, the sheet member 20 extends radially from the central region of the fovea beyond the perimeter boundary of the parafoveal area of a macula. Other embodiments are contemplated wherein the cover may be sized to cover different sized regions of the central macula.

The sheet member 20 is radially sloped toward the perimeter 190. The radial sloping of the sheet member 20 is defined by a sloping convex surface 140 that extends between the central tab 150 to the perimeter 190 of the sheet member 20.

The bioadhesive region 170 is a flat, perimeter region of the inner surface 130 of the sheet member 20 between the inner surface 130 and the perimeter 190. The bioadhesive region 170 is positionable over and in contact with the surface of the parafoveal area of the macula. When the sheet member 20 in placed over the fovea and parafoveal area of the macula, the bioadhesive region 170 makes direct contact with the surface of the parafoveal area of the macula and sits directly in contact with the inner surface of the parafoveal area of the macula. As the bioadhesive region 170 comes in contact with the inner surface of the parafoveal area, the sheet member 20 flexes upward so as not to contact the inner surface of the foveal area. The radial elements 160 provide upward pressure on the sheet member 20 keeping the sheet member 20 from contacting the inner surface of the fovea. The only point of contact between the sheet member 20 and the macula surface occurs between the bioadhesive region 170 and the parafoveal area of the macula.

The central tab 150 of the macula cover 120 is attached at the central region of the convex surface 140 of the sheet member 20. The central tab 150 is rectangularly shaped and extends vertically from the central region of the convex surface 140. In use, the central tab 150 is designed to aid in the insertion and the removal of the macular cover 120 during a surgical procedure.

The radial elements 160 of the sheet member 20 are designed to provide a stiffening region that will maintain the macula cover 120 in a fully extended configuration. The radial elements 160 are a region of the sheet member 20 that have increased strength and density with more rigid characteristics than the area of the sheet member 20 adjacent to the radial elements 160. Generally, the radial elements 160 are radially aligned in the sheet member 20 to extend an area of stiffness from the central tab 150 to the perimeter 190 of the sheet member 20 of the macula cover 120.

The bioadhesive region 170 has a coating of bioadhesive material located on the perimeter of the inner surface 130. The bioadhesive region 170 aids in maintaining the position of the macula cover 120 over the macula by forming an adhesive bond between the bioadhesive region 170 and the parafoveal area of the macula. The bioadhesive region 170 forms an adhesive force between the macula cover 120 and the inner surface of the parafoveal area of the macula that is capable of withstanding 0.1 to 1 dynes/cm$^2$ of shear force that may be created by the fluid forces around the macula.

In the umbrella model, the macula cover 120 can be made from material that is a thin, light, and opaque biocompatible material. As the surgeon removes the internal limiting membrane, the macula cover 120 can be removed with a vitreous cutting instrument, or it can be pulled into the injector 70.

During the surgical procedure, the surgeon typically injects fluid into the eye. If the fluid is injected directly toward the macula cover 120, the bioadhesive region 170 will maintain the position of the macula cover 120 over the fovea and parafoveal area of the macula during surgical irrigation by forming a bond between the inner surface of the parafoveal area of the macula and the bioadhesive region 170 of the macula cover 120.

Figure 14:
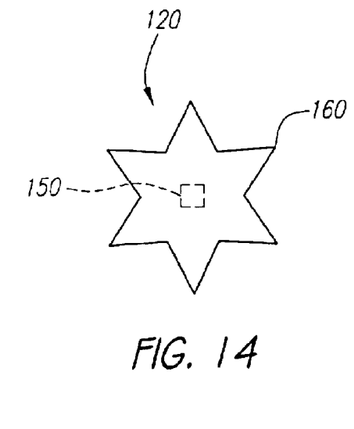
FIG. 14 is a side view of a macula cover compressed in an umbrella configuration that allows the placement of the macula cover within the injector.
Figure 15:
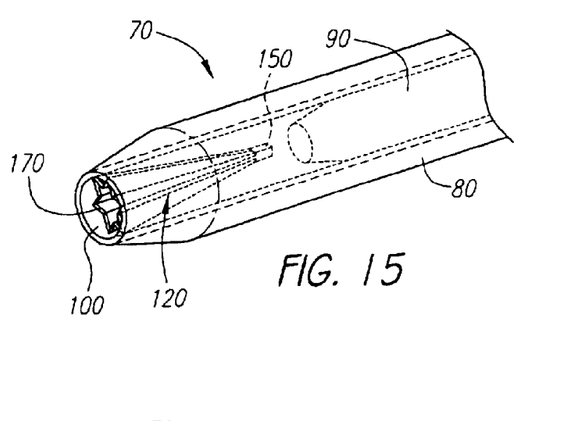
FIG. 15 is a perspective view of the injector with the macula cover in an umbrella configuration contained within the injector.
Figure 16:
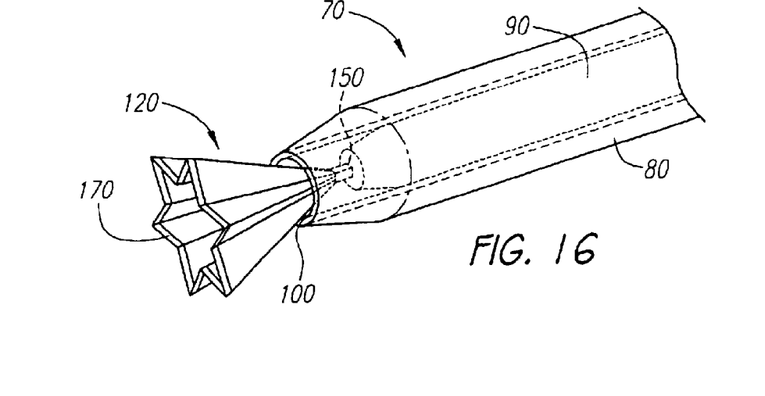
FIG. 16 is a perspective view of the injector with the macula cover in an umbrella configuration exiting the injector and the injector rod partially deployed.
Figure 17:
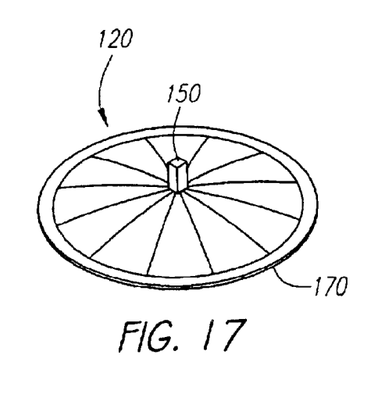
FIG. 17 is perspective view of a macula cover in an umbrella configuration after the macula cover has exited the injector.
Figure 18:
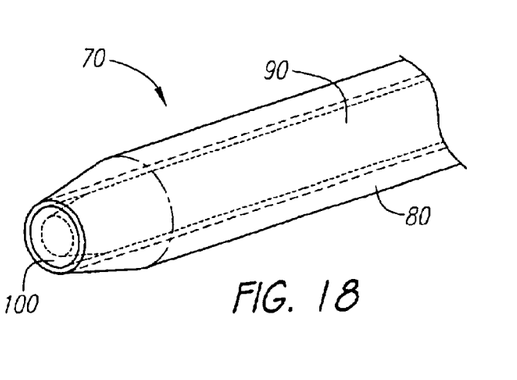
FIG. 18 is perspective view of the injector and the injector rod fully deployed.

When the macula cover 120 is placed in the eye through an injector 70, the macula cover 120 is collapsed upon itself in a configuration that resembles a closed umbrella along an axis that allows the macula cover 120 to be placed within the hollow tube 80 of the injector 70. This configuration positions the macula cover 120 so that the inner surface 130 is completely enclosed from making contact with any external surface. When the macula cover 120 is pushed through the hollow tube 80 by the injector rod 90, the macula cover exits through the opening 100 of the hollow tube 80 in the compressed umbrella configuration. The radial elements 160 are designed to aid in the expansion of the macula cover 120 by providing a spring effect to the sheet member 20. As the sheet member 20 begins to expand to a fully extended position, the radial elements 160 maintain the fully extended umbrella configuration by providing stiff regions that prevent the sheet member 20 of the macula cover 120 from folding over upon itself.

As shown in FIGS. 14–20 the macula cover 120 can be part of a surgical tool kit that includes the macula cover 120 and an injector 70. The injector includes a hollow tube 80, an injector rod 90, an opening 100, and an injector forceps 180. The hollow tube 80 is sized to contain the macula cover 120 when the macula cover 120 is collapsed upon itself in an umbrella configuration. In the umbrella configuration, the macula cover 120 can be inserted into the hollow tube 80 by placing the central tab 150 into the opening 100 of the hollow tube 80 and pulling the macula cover 120 into the hollow tube 80 by activating the injector forceps 180. In the umbrella configuration, the macula cover 120 collapses over the contact surface 130 leaving the central tab 150 and the convex surface 140 as the only surfaces exposed to the interior of the hollow tube 80. After the injector 70 has been positioned within the eye over the area of the macula, the surgeon can manipulate the injector 70 to move the injector rod 90 longitudinally within the hollow tube 80. As the injector rod 90 moves longitudinally within the hollow tube 80, the injector rod 90 makes contact with the central tab 150 of the macula cover 120 and moves the macula cover 120 toward the end of the hollow tube 80 of the injector 70. In the umbrella configuration, the macula cover 120 can move within the hollow tube 80 of the injector 70 without making contact between the inner surface 130 of the macula cover 120 and the hollow tube 80. The end of the hollow tube 80 has an opening 100 that allows the macula cover 120 to pass out of the interior of the hollow tube 80. As the macula cover 120 exits the opening 100 of the hollow tube 70, the radial elements 160 provide outward pressure to the sheet member 20 and the macula cover 120 opens in an umbrella like manner. As the surgeon positions the macula cover 120 and the macula cover 120 opens to a completely expanded configuration, the bioadhesive region 170 of the inner surface 130 makes contact with the inner surface of the parafoveal area of the macula. This contact forms a bond between the bioadhesive region 170 and the inner surface of the parafoveal area and the macula cover 120 remains in that location until the surgeon decides to remove it, or until it is peeled away during internal limiting membrane removal.

Figure 19:
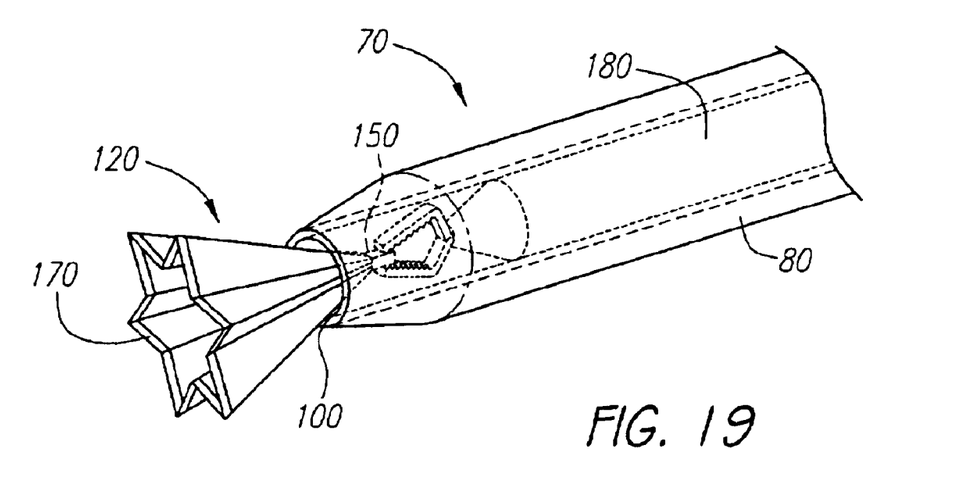
FIG. 19 is perspective view of a macula cover in an umbrella configuration entering the injector and the injector forceps partially deployed.
Figure 20:
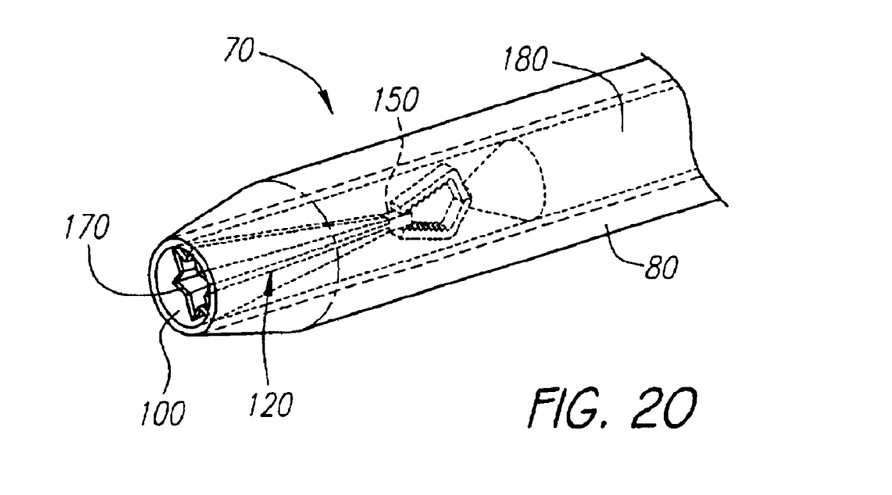
FIG. 20 is a perspective view of the injector with the macula cover in an umbrella configuration contained within the injector with the injector forceps fully retracted.

As shown in FIGS. 19 and 20, when the macula cover 120 has been inserted into the interior of the eye, and the surgeon completes surgery, he can remove the macula cover 120 by replacing the injector rod 90 with the injector forceps 180 and grabbing the central tab 150 and pulling the macula cover 120 into the interior of the hollow tube 80 of the injector 70.

Figure 11:
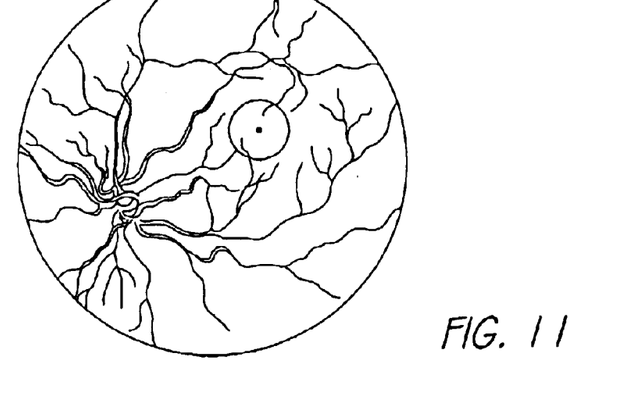
FIG. 11 is a side view of the interior of the eye with the macula cover placed over the macula before the interior of the eye has been stained with Indocyanine Green dye.
Figure 12:
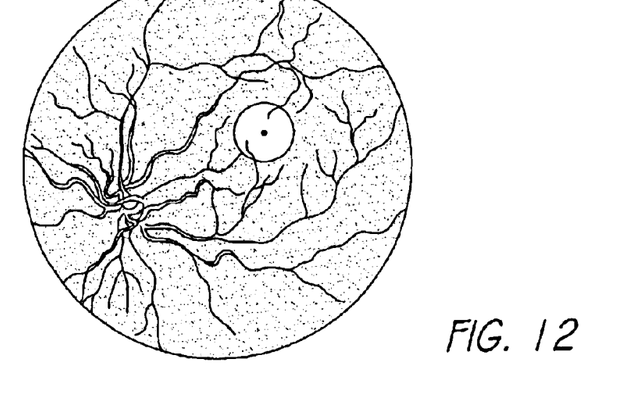
FIG. 12 is a side view of the interior of the eye with macula cover placed over the macula after the interior of the eye has been stained with Indocyanine Green dye.
Figure 13:
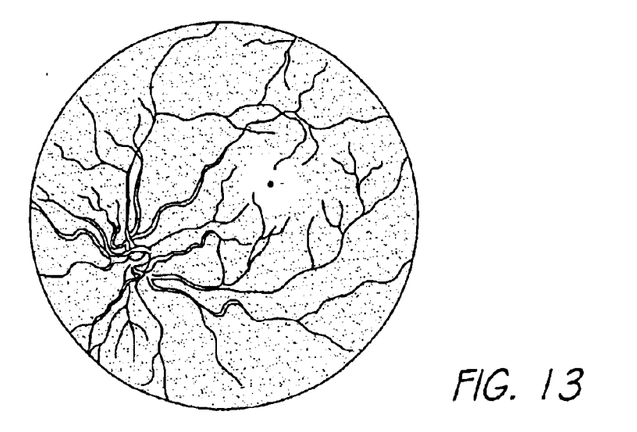
FIG. 13 is a side view of the interior of the eye with the macula cover removed after the interior of the eye has been stained with Indocyanine Green dye.

In operation, macula covers 10, 120 protect the ocular surgical patient by creating a physical barrier over the surface of the fovea and parafoveal area of the macula. When a macula cover 10, 120 are positioned aver the surface of the fovea and parafoveal area of the macula, a macula cover 10, 120 extends a physical barrier horizontally from the central region of the fovea beyond the perimeter of the parafoveal region of the macula. This layer of protection prevents Indocyanine dye from penetrating the tissues covered by a macula cover 10, 120. When a surgeon attempts to remove the internal limiting membrane of the retina to reduce traction in the macula, the surgeon routinely uses Indocyanine Green dye to stain internal limiting membrane. As shown in FIGS. 11–13, when Indocyanine Green dye is placed in contact with the internal limiting membrane, a macula cover 10, 120 is designed to provide a physical barrier that impedes the flow of the dye. If there are any defects in the internal limiting membrane such as with a macular hole, the ICG dye can penetrate into the neurosensoly retina arid the retinal pigment epithelium. When a macula cover 10, 120 is positioned over and in contact with the fovea and parafoveal area of the macula, the dye is impeded from flowing into the central macula by the physical barrier of a macula cover 10, 120. Macula covers 10, 120 prevent Indocyanine dye from flowing through the internal limiting membrane and this aids in the prevention of potential chemical toxicity that may be caused by the penetration of the Indocyanine Green dye into neurosensory retina or the retinal pigment epithelium.

Macula covers 10, 120 also provides a physical barrier that prevents light waves from making contact with the surface of the macula. During eye surgery, the surgeon illuminates the interior of the eye by using a fiber optic probe that emits light waves that can make direct, unimpeded contact with the surface of the fovea and parafoveal area of the macula. When a macula cover 10, 120 is placed over and in contact with the fovea and parafoveal area of the macula, a macula cover 10, 120 prevents light waves from reaching the tissues of the macula covered by a macula cover 10, 120 by absorbing incoming light waves into the sheet member 20 of a macula cover 10, 120. This design allows a macula cover 10, 120 to advantageously protect the patient from any potential damage that may be caused by exposure to excess light. Additionally, this protection may provide the surgeon with additional time to complete the surgical procedure.

Thus, the improved ocular procedures and devices are disclosed. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A macula cover, comprising
a flexible sheet member including a contact surface, an outer surface, a perimeter, and an annular stiffener, the sheet member being sized to cover a fovea and parafoveal area of a macula and being radially tapered toward the perimeter with the perimeter defining a knife edge, the contact surface being positionable over and in contact with the surface of the fovea and parafoveal area of the macula.

2. The macula cover of claim 1 further comprising a tab attached at the periphery of the tab to the periphery of the sheet member.

3. The macula cover of claim 1, the sheet member further being of an opaque material.

4. The macula cover of claim 1, the annular stiffener further including a
circular ridge and a sloping surface extending between the circular ridge and the perimeter.

5. The macula cover of claim 1, the outer surface further being concave.

6. The macula cover of claim 1, the sheet member further being of a combination of dense material and lightweight material.

7. A macula cover, comprising
a flexible sheet member including a contact surface, an outer surface, a perimeter, and an annular stiffener, the sheet member being sized to cover a fovea and parafoveal area of a macula and being radially tapered toward the perimeter with the perimeter defining a knife edge and being of an opaque material, the contact surface being positionable over and in contact with a surface of the fovea and parafoveal area of the macula, the annular stiffener including a circular ridge and a sloping surface extending between the circular ridge and the perimeter.

8. The macula cover of claim 7, the outer surface further being concave.

9. The macula cover of claim 7 further comprising a tab attached at the periphery of the tab to the periphery of the sheet member.

10. The macula cover of claim 7, the sheet member further being of a combination of dense material and lightweight material.

11. A macula cover, comprising
a flexible sheet member including a convex surface, an inner surface, a bioadhesive region, a perimeter, a central tab, and a plurality of radial elements, the sheet member being made from an opaque material and being sized to cover a fovea and parafoveal area of a macula, the convex surface being radially sloped toward the perimeter with the perimeter defining an edge, the inner surface being positionable over the fovea and parafoveal area of the macula, the bioadhesive region including a coating of a bioadhesive material on the perimeter of the inner surface of the sheet member, the central tab being attached to the center of the convex surface and extending upward from the convex surface, and the radial elements being a region of stiffness extending radially from the center of the sheet member to the perimeter.

12. A surgical tool kit, comprising
a macula cover including a flexible sheet member including a contact surface, an outer surface, a perimeter, and an annular stiffener, the sheet member being sized to cover the fovea and parafoveal area and being radially tapered toward the perimeter with the perimeter defining a knife edge, the contact surface being positionable over and in contact with the surface of the macula; and
an injector, including a hollow tube, an opening, and an injector rod, the hollow tube sized to contain the cover rolled about an axis extending longitudinally of the hollow tube, the opening being positioned on one end of the hollow tube and sized to allow the passage of the cover, the injector rod being longitudinally movable and positioned inside the hollow tube to contact the cover and move the cover through the opening.

13. A surgical tool kit, comprising
a macula cover including a flexible sheet member including a convex surface, an inner surface, a bioadhesive region, a perimeter, a central tab, and a plurality of radial elements, the sheet member being made from an opaque material and being sized to cover a fovea and parafoveal area of a macula, the convex surface being radially sloped toward the perimeter with the perimeter defining an edge, the inner surface being positionable over the fovea and parafoveal area of the macula, the bioadhesive region including a coating of a bioadhesive material on the perimeter of the inner surface of the sheet member, the central tab being attached to the center of the convex surface and extending upward from the convex surface, and the radial elements being a region of stiffness extending radially from the center of the sheet member to the perimeter, and
an injector, including a hollow tube, an opening, an injector rod, and an injector forceps, the hollow tube sized to contain the cover collapsed over the inner surface in an umbrella configuration and the convex surface and central tab exposed extending longitudinally of the hollow tube, the opening being positioned on one end of the hollow tube and sized to allow the passage of the cover, the injector rod being longitudinally movable and positioned inside the hollow tube to contact the cover and move the cover through the opening, and the injector forceps being longitudinally movable and positioned inside the hollow tube to grasp the central tab of the cover and move the cover through the opening into the hollow tube.

* * * * *